United States Patent
LeClerc et al.

(10) Patent No.: US 7,972,860 B2
(45) Date of Patent: Jul. 5, 2011

(54) METHODS AND COMPOSITIONS FOR THE DETECTION AND ANALYSIS OF NUCLEIC ACIDS BY SIGNAL AMPLIFICATION

(75) Inventors: Mario LeClerc, Quebec (CA); Hoang-Anh Ho, Sainte-Foy (CA)

(73) Assignee: National Research Council of Canada, Ottawa (CA)

( * ) Notice: Subject to any disclaimer, the term of this patent is extended or adjusted under 35 U.S.C. 154(b) by 335 days.

(21) Appl. No.: 11/817,482

(22) PCT Filed: Mar. 3, 2006

(86) PCT No.: PCT/CA2006/000322
§ 371 (c)(1),
(2), (4) Date: Apr. 2, 2008

(87) PCT Pub. No.: WO2006/092063
PCT Pub. Date: Sep. 8, 2006

(65) Prior Publication Data
US 2009/0215187 A1    Aug. 27, 2009

Related U.S. Application Data

(60) Provisional application No. 60/657,717, filed on Mar. 3, 2005.

(51) Int. Cl.
*G01N 33/50* (2006.01)
*C07H 21/00* (2006.01)
(52) U.S. Cl. .................. 436/94; 250/458.1; 536/24.3
(58) Field of Classification Search .............. 436/94; 536/24; 250/458.1
See application file for complete search history.

(56) References Cited

U.S. PATENT DOCUMENTS

| 5,780,610 A | 7/1998 | Collins |
| 6,197,949 B1 | 3/2001 | Teoule et al. |
| 6,589,731 B1 | 7/2003 | Chen et al. |

(Continued)

FOREIGN PATENT DOCUMENTS

WO    WO 98/03499    1/1998

(Continued)

OTHER PUBLICATIONS

Dore et al. "Fluorescent polymeric transducer for the rapid, simple, and specific detection of nucleic acids at the zeptomole level" J. Am. Chem. Soc., 126(13), pp. 4240-4244 (2004).

(Continued)

*Primary Examiner* — Krishnan S Menon
*Assistant Examiner* — Rebecca Fritchman
(74) *Attorney, Agent, or Firm* — Milbank Tweed Hadley & McCloy, LLP

(57) ABSTRACT

The present invention relates to a novel integrated PCR-free signal amplification polynucleotide detection system which combines a specific receptor, an optical transducer, and an amplification mechanism. This novel detection system is based on different electrostatic interactions and confirmations between a cationic polythiophene (i.e., polymer 1) and single-stranded or double-stranded polynucleotides (such as ss-DNA or ds-DNA), and the efficient energy transfer between the triplex (complexation between the cationic polythiophene and ds-DNA) and neighboring fluorophores attached to ss-DNA or ds-DNA probes. It is to be understood that in the case of ss-DNA, triplex formation occurs via the hybridization of complementary ss-DNA strands, combined with complexation and with the cationic polythiophene. The present detection system allows for the detection of single nucleotide polymorphisms (SNPs) from samples in only a few minutes, without the need for nucleic acid amplification.

13 Claims, 7 Drawing Sheets

U.S. PATENT DOCUMENTS

| | | |
|---|---|---|
| 7,214,489 B2 | 5/2007 | Bazan et al. |
| 7,270,956 B2 | 9/2007 | Bazan et al. |
| 2004/0142206 A1 | 7/2004 | Bazan et al. |
| 2005/0003386 A1 | 1/2005 | Bazan et al. |

FOREIGN PATENT DOCUMENTS

| | | |
|---|---|---|
| WO | WO 02/081735 | 10/2002 |

OTHER PUBLICATIONS

Nilsson et al. "Chip and solution detection of DNA hybridization using a luminescent zwitterionic polythiophene derivative" Nat. Mater., 2(6), pp. 419-424 (2003).

Drummond et al. "Electrochemical DNA sensors" Nature Biotechnology, 21(10), pp. 1192-1199 (2003).

Kim et al. "Control of conformational and interpolymer effects in conjugated polymers" Nature, 411, pp. 1030-1034 (2001).

Leach et al. "Theoretical investigation of novel nucleic acid bases" J. Am. Chem. Soc., 114(10), pp. 3675-3683 (1992).

Levitsky et al. "Energy migration in poly(phenylene ethynylene): Determination of interpolymer transport in anisotropic Langmuir-Blodgett films" J. Am. Chem. Soc., 121(7), pp. 1466-1472 (1999).

Liu et al. "Homogenous fluorescence-based DNA detection with water-soluble conjugated polymers" Chem. Mater., 16(23), pp. 4467-4476 (2004).

Liu et al. "Self-contained, fully integrated biochip for sample preparation, polymerase chain reaction amplification, and DNA microarray detection" Anal. Chem., 76(7), pp. 1824-1831 (2004).

McQuade et al. "Signal amplification of a 'turn-on' sensor: Harvesting the light captured by a conjugated polymer" J. Am. Chem. Soc., 122(49), pp. 12389-12390 (2000).

Nam et al. "Bio-bar-code-based DNA detection with PCR-like sensitivity" J. Am. Chem. Soc., 126(19), pp. 5932-5933 (2004).

Phaneuf et al. "Type 1 hereditary tyrosinemia. Evidence for molecular heterogeneity and identification of a causal mutation in a French Canadian patient" J. Clin, Invest. 90, pp. 1185-1192 (1992).

Piccirilli et al. "Enzymatic incorporation of a new base pair into DNA and RNA extends the genetic alphabet" Nature, 343, pp. 33-37 (1990).

Saiki et al. "Enzymatic amplification of β-globin genomic sequences and restriction site analysis for diagnosis of sickle cell anemia" Science, 230, pp. 1350-1354 (1985).

St-Louis et al. "Mutations in the fumarylacetoacetate hydrolase gene causing hereditary tyrosinemia type 1: overview" Human Mutation 9, pp. 291-299 (1997).

Switzer et al. "Enzymatic recognition of the base pair between isocytidine and isoguanosine" Biochemistry, 32(39), pp. 10489-10496 (1993).

Tor et al. "Site-specific enzymatic incorporation of an unnatural base, $N^6$-(6-aminohexyl)isoguanosine, into RNA" J. Am. Chem. Soc., 115(11), pp. 4461-4467 (1993).

Mantsch et al. "Structural and enzymatic properties of adenine 1-oxide nucleotides" Biochemistry. 14(26), pp. 5593-5601 (1975).

Beljonne, D., et al., Interchain vs. intrachain energy transfer in acceptor-capped conjugated polymers, Proc. Natl. Acad. Sci. U.S.A. 99, 10982-10987 (2002).

Chen, L., et al., Highly sensitive biological and chemical sensors based on reversible fluorescence quenching in a conjugated polymer, Proc. Natl. Acad. Sci. U.S.A. 96, 12287-12292 (1999).

Daar, A.S., et al., Top ten biotechnologies for improving health in developing countries, Nat. Genet. 32, 229-232 (2002).

Fodor, S.P.A., et al., Light-directed spatially addressable parallel chemical synthesis, Science 251, 767-773 (1991).

Gaylord, B.S., et al., DNA detection using water-soluble conjugated polymers and peptide nucleic acid probes. Proc. Natl. Acad. Sci. U.S.A. 99, 10954-10957 (2002).

Ho, H.A., et al., Colorimetric and fluorometric detection of nucleic acids using cationic polythiophene derivatives., Angew. Chem. Int. Ed. 41, 1548-1551 (2002).

Leclerc, M., Optical and electrochemical transducers based on functionalized conjugated polymers, Adv. Matter. 11, 1491-1498 (1999).

McQuade, D.T., et. al., Conjugated polymer-based chemical sensors, Chem. Rev. 100, 2537-2574 (2000).

Nguyen, T.-Q., et al., Control of energy transfer in oriented conjugated polymer-mesoporous silica composites, Science 288, 652-656 (2000).

Tyagi, S. & Kramer, F.R., Molecular beacons: probes that fluoresce upon hybridization, Nat. Biotechnology 14, 303-308 (1996).

US 7,972,860 B2

METHODS AND COMPOSITIONS FOR THE DETECTION AND ANALYSIS OF NUCLEIC ACIDS BY SIGNAL AMPLIFICATION

CROSS-REFERENCE TO RELATED APPLICATIONS

The present application is a U.S. National Phase Application of International Application No. PCT/CA2006/000322, filed Mar. 3, 2006, which claims the benefit of U.S. Provisional Application No. 60/657,717, filed Mar. 3, 2005, both of which are hereby incorporated by reference in their entireties.

FIELD OF THE INVENTION

The present invention relates to methods, articles and compositions for the detection and analysis of nucleic acids in a sample. More specifically, the invention relates to a novel integrated polymerase chain reaction (PCR)-free signal amplification polynucleotide detection system which combines a specific receptor, an optical transducer, and an amplification mechanism. The system of the present invention is highly sensitive, allowing for the specific detection of oligonucleotides and polynucleotides present in small quantities (i.e., in as few as approximately 20 copies).

BACKGROUND OF THE INVENTION

Simple and ultra sensitive sequence-specific DNA biosensors are needed for the rapid diagnostic of infections and genetic diseases, as well as for environmental and forensic applications.[1] For this purpose, various optical and electrochemical DNA sensors have been proposed.[2-8] However, most of these proposed DNA sensors rely on some form of chemical amplification, such as PCR,[9] which in turn can require the use of complex mixtures and sophisticated hardware to perform the necessary enzymatic reactions.

More recently, rapid fluorescence-based DNA detection methods based on water-soluble conjugated cationic polymers have been described.[10-14, 23-26] Here, a polycationic polymer is used as a light-harvesting multichromophore (see, for example, United States Patent Application Publication No. US 2004/0219556 A1 (Nov. 4, 2004) (Bazan et al.)). A sensor based on a neutral peptide nucleic acid (PNA) and having a signaling chromophore having a base sequence complementary to a target polynucleotide of interest is provided. Upon contacting the target polynucleotide in a sample, the polycationic multichromophore is brought into proximity with the signaling chromophore by virtue of electrostatic interactions with the target polynucleotide. Excitation of the multichromophore then produces light emission from the signaling chromophore. While this method provides for a quick and reliable way to measure the quantity of polynucleotides in a sample, it does not by itself allow for the detection of very minute quantities of nucleotides in the sample.

There thus remains a need for a method allowing for the rapid and highly-sensitive detection of polynucleotides in a sample without resorting to nucleotide amplification techniques, such as PCR. Moreover, there remains a need for compositions and articles of manufacture useful in such a method.

The present invention seeks to meet these and other needs.

SUMMARY OF THE INVENTION

The present invention relates to a method providing for the rapid and specific detection of single-stranded or double-stranded oligonucleotides and polynucleotides, and to compositions and articles of manufacture useful to perform such methods.

The present invention further relates to a method providing for the rapid and specific detection of single-stranded or double-stranded oligonucleotides and polynucleotides in samples, and to compositions and articles of manufacture useful to perform such methods.

In an embodiment, the present invention relates to a nucleic acid detection system comprising an anionic oligonucleotide probe, a water-soluble conjugated cationic polymeric transducer, and an intrinsic photonic amplification mechanism. The water-soluble conjugated cationic polymeric transducer also serves as a localized counter-ion, promoting specific hybridization. Moreover, the polymeric transducer, when combined with capture probes labeled with a fluorophore, provides for signal amplification and improved detection limits.

The nucleic acid detection system of the present invention is capable of specifically and rapidly detecting as few as 20 single-stranded oligonucleotides. In an embodiment of the present invention, the single-stranded oligonucleotides to be detected may be extracted from clinical samples.

Advantageously, the nucleic acid detection system of the present invention is suitable for rapidly assessing the identity of single nucleotide polymorphisms (SNPs), genes, and pathogens without the need for nucleic acid amplification.

In an embodiment, the present invention relates to a nucleic acid detection system comprising a water-soluble affinity-chromic cationic polythiophene; an anionic oligonucleotide capture probe labeled with a fluorophore to form a duplex with the water-soluble affinitychromic cationic polythiophene; and a sample suspected of containing a complementary target oligonucleotide.

In an embodiment, the present invention relates to a method for detecting short length nucleic acid molecules comprising: providing a water-soluble affinitychromic cationic polythiophene; contacting the water-soluble affinitychromic cationic polythiophene with an anionic oligonucleotide capture probe labeled with a fluorophore to form a duplex; and contacting the duplex with a sample suspected of containing a complementary target oligonucleotide.

Further scope and applicability will become apparent from the detailed description given hereinafter. It should be understood, however, that this detailed description, while indicating preferred embodiments of the invention, is given by way of example only, since various changes and modifications will become apparent to those skilled in the art.

DEFINITIONS AND TERMS

Figure 1:
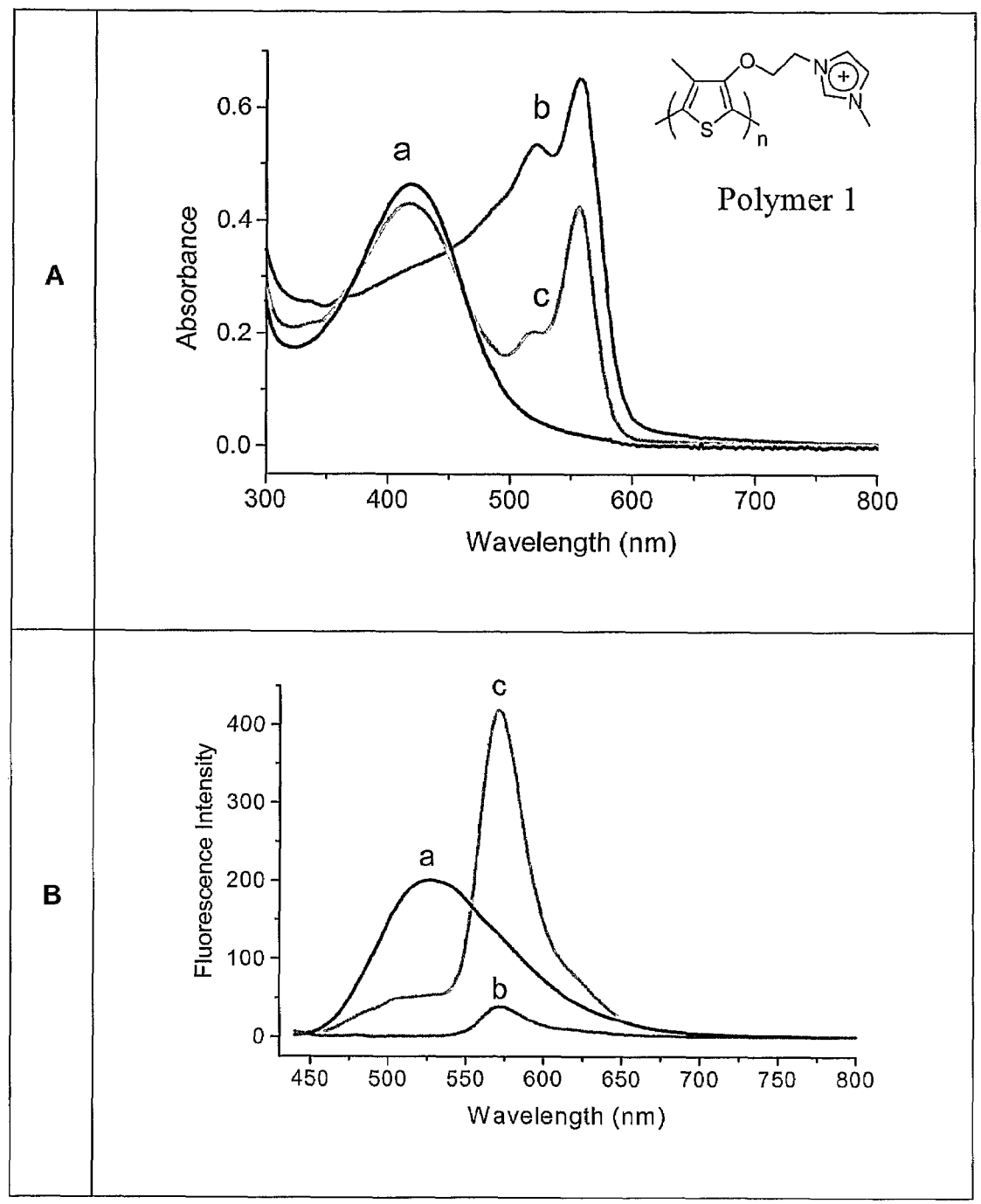
FIG. 1 illustrates: A. Chemical structure of polymer 1 and UV-visible absorption spectra of (a) polymer 1/X1/Y1 triplex (perfect match), (b) polymer 1/[X1+Alexa Fluor (AF) 546] duplex, and (c) polymer 1/X1+AF546/Y1 triplex (perfect match) in water at 55° C. B. Fluorescence spectra, with excitation at 420 nm, of (a) polymer 1/X1/Y1 triplex (perfect match), (b) polymer 1/[X1+AF546] duplex; (c) polymer 1/X1+AF546/Y1 triplex (perfect match) in water at 55° C.

The terminology used herein is for the purpose of describing particular embodiments only and is not intended to limit the scope of the present invention.

Use of the singular forms "a," "an," and "the" include plural references unless the context clearly dictates otherwise. Thus, for example, reference to "a target polynucleotide" includes a plurality of target polynucleotides.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

Terms such as "connected," "attached," and "linked" may be used interchangeably herein and encompass direct as well as indirect connection, attachment, linkage or conjugation unless the context clearly dictates otherwise.

Where a value is explicitly recited, it is to be understood that values which are about the same quantity or amount as the recited value are also within the scope of the invention, as are ranges based thereon.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. These terms refer only to the primary structure of the molecule. Thus, the terms include triple-, double- and single-stranded deoxyribonucleic acid ("DNA"), as well as triple-, double- and single-stranded ribonucleic acid ("RNA"). They also include modified (for example, by alkylation and/or by capping) and unmodified forms of the polynucleotide.

More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing a phosphate or other polyanionic backbone, and other synthetic sequence-specific nucleic acid polymers provided that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, and hybrids thereof, including, for example, hybrids between DNA and RNA, and also include known types of modifications, for example, labels, alkylation, "caps," substitution of one or more of the nucleotides with an analog, internucleotide modifications such as, for example, those with negatively charged linkages (e.g., phosphorothioates, phosphorodithioates, etc.), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

As used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Additionally, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide; preferably the polynucleotide does not comprise abasic sites. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-.beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidine) to form isocytosine (1-.beta.-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described in U.S. Pat. No. 5,780,610 to Collins et al. Other normatural base pairs may be synthesized by the method described in Piccirilli et al. (1990) Nature 343:33-37 for the synthesis of 2,6-diaminopyrimidine and its complement (1-methylpyrazolo-[4,3]pyrimidine-5,7-(4H,6H)-dione). Other such modified nucleotidic units which form unique base pairs are known, such as those described in Leach et al. (1992) J. Am. Chem. Soc. 114:3675-3683 and Switzer et al., supra.

Hybridization conditions will typically include salt concentrations of less than about 1M, more usually less than about 500 mM and preferably less than about 200 mM. Hybridization temperatures can be as low as 5.degree. C., but are typically greater than 22.degree. C., more typically greater than about 30.degree. C., and preferably in excess of about 37.degree. C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Suitable hybridization conditions for a given assay format can be determined by one of skill in the art; nonlimiting parameters which may be adjusted include concentrations of assay components, salts used and their concentration, ionic strength, temperature, buffer type and solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multi-parametric determination" herein refers to an assay or other analytical method in which multiple analytes can be assayed simultaneously.

The sample comprising or suspected of comprising the target polynucleotide can be any source of biological material which comprises polynucleotides that can be obtained from a living organism directly or indirectly, including cells, tissue or fluid, and the deposits left by that organism, including viruses, mycoplasma, and fossils. The sample may comprise a target polynucleotide prepared through synthetic means, in whole or in part. Typically, the sample is obtained as or dispersed in a predominantly aqueous medium. Nonlimiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant library comprising polynucleotide sequences.

The sample can be diluted, dissolved, suspended, extracted or otherwise treated to solubilize and/or purify any target polynucleotide present or to render it accessible to reagents which are used in an amplification scheme or to detection reagents. Where the sample contains cells, the cells can be lysed or permeabilized to release the polynucleotides within the cells. One step permeabilization buffers can be used to lyse cells which allow further steps to be performed directly after lysis, for example, a polymerase chain reaction.

The target polynucleotide can be single-stranded, double-stranded, or higher order, and can be linear or circular. Exemplary single-stranded target polynucleotides include MRNA, rRNA, tRNA, hnRNA, ssRNA or ssDNA viral genomes, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phage, and viroids. The target polynucleotide can be prepared synthetically or purified from a biological source. The target polynucleotide may be purified to remove or diminish one or more undesired components of the sample or to concentrate the target polynucleotide. Conversely, where the target polynucleotide is too concentrated for the particular assay, the target polynucleotide may be diluted.

Experimental

Materials. Polymer 1 was synthesized according to previously published work.[10,13] On the basis of size-exclusion chromatography measurements calibrated with monodisperse polyvinylpyridinium samples, the polymer had a number-average molecular weight of 11000 with a polydispersity index of 2.0. Labeled and unlabeled oligonucleotides were purchased from Integrated DNA Technologies, Inc. For studies on 20-mer oligonucleotides, the probe (X1) and targets (Y1, Y2, and Y3) were derived from probes designed for the detection of Candida yeast species.[10] For the detection of tyrosinemia type I IVS12+5 G->A splice mutation[21], the 15-mer capture probe sequence complementary to the mutated sequence in the genome was (TAN 100) 5'-CCG GTG AAT ATC TGG-3', and the capture probe complementary to wild type DNA was (TAN 101) 5'-CCG GTG AGT ATC TGG-3'. Alexa Fluor 546 was attached to the 5'-end of the oligonucleotide probes. All oligonucleotides solutions were diluted with sterilized water, and all dilutions and solution handlings were performed in plasticware.

Extraction and purification of DNA from blood. Human genomic DNA was extracted from patient blood as previously described[22] and stored frozen at −20° C. until use.[22]

General procedure for optical measurements. UV-visible absorption spectra (FIG. 1A) were recorded using a Hewlett-Packard (model 8452A) spectrophotometer. Fluorescence spectra (FIG. 1B) were recorded using a Varian Cary Eclipse spectrofluorometer. The fluorescence calibration curves (FIGS. 2 and 4) were obtained using a custom portable fluorometer[13] modified for measurement of the Alexa Fluor emission at 572 nm. In all cases, excitation was performed at 420 nm, and the fluorescence data points on the calibration curves were obtained from the average of 5 optical measurements at 572 nm. Each optical measurement was obtained by the integration of the fluorescence signal over a period of 10 seconds. For all optical measurements, 3-mL quartz cells with an optical path length of 1.0 cm were utilized. The detection limit was calculated as being 3 times the standard deviation of the optical measurements for the blank signal divided by the slope of the calibration curve. Duplexes were prepared by mixing stoichiometric quantities of the polymer and of the oligonucleotide capture probe to give a concentration of 2.14 µM (stock solution). The resulting complex was then diluted to the desired concentrations. Hybridization experiments were carried out at 55° C. for the 20-mer oligonucleotides and at 65° C. for the detection of tyrosinemia SNPs. For the tyrosinemia studies, the samples were first denatured at 100° C.

Preparation of 150 bp amplicons of a portion of the EF-1a gene from C. albicans and C. dubliniensis. 350 pg of genomic DNA preparation at a concentration of 350 pg/µl was transferred into a 19-µl PCR mixture containing 50 mM KCl, 10 mM Tris-HCl (pH 9.1), 0.1% Triton X-100, 2.5 mM MgCl2, 0.4 µM concentrations of primers ECal61 [5'-CAAGAAG-GTTGGTTACAACCCAAAGA-3'] and Ecal184 [5'-AG-GTCTTACCAGTAACTTTACCGGAT-3']), 200 µM deoxynucleoside triphosphate (Amersham Biosciences, Piscataway, N.J.), 3.3 µg of bovine serum albumin (Sigma-Aldrich Canada Ltd., Oakville, Ontario, Canada) per µl, and 0.025 U of Taq DNA polymerase (Promega, Madison, Wis.) combined with the TaqStart antibody (BD Biosciences Clontech, Palo Alto, Calif.). The PCR mixtures were subjected to thermal cycling (3 min at 95° C. and then 40 cycles of 30 sec at 95° C. for the denaturation step, 30 sec at 55° C. for the annealing step and 30 sec at 72° C. for the extension step) on a PTC-200 thermal cycler (MJ Research Inc., Watertown, Mass.). PCR amplification products were purified by QIAquick Gel Extraction Kit (Qiagen Inc., Mississauga, Ontario, Canada) using deionized water for eluting the amplicons.

Purification of DNA from the blood of human healthy volunteers. 7 ml of blood were drawn from healthy volunteers using Vacutainer™ tubes containing (K3) EDTA (Lavender caps, order number 366450, Becton Dickinson). 200 µL of this blood were used for DNA extraction and purification using the MagneSil KF Genomic System (Cat no. MD1460) from Promega. The sample preparations were performed according to the manufacturer's instructions (MagneSil™ KF Genomic System, MD1460rev01) except for one slight modification: in step IVb of the Promega protocol, 200 µL of TE were used instead of 200 µl of nuclease-free water. The magnetic particles were handled using a KingFisher™ mL magnetic particle processor from Thermo Labsystems driven by the "PromegaGenomic" program Version 1.0 (Magne-Sil™ KF genomic system, program downloaded from the Promega web site as "KfmLMagGenomv1_0").

DETAILED DESCRIPTION

The present invention relates to a novel integrated PCR-free signal amplification DNA detection system which combines a specific receptor, an optical transducer, and an amplification mechanism. This novel detection system is based on different electrostatic interactions and conformations between a cationic polythiophene (i.e. polymer 1) and ss-DNA or ds-DNA, and the efficient energy transfer between the triplex (complexation between the cationic polythiophene and ds-DNA) and neighboring fluorophores attached to ss-DNA or ds-DNA probes. It is to be understood that in the case of ss-DNA, triplex formation occurs via the hybridization of complementary ss-DNA strands, combined with complexation with the cationic polythiophene. The present detection system allows for the detection of single nucleotide polymorphisms (SNPs) from clinical samples in only a few minutes, without the need for nucleic acid amplification. In a further embodiment of the present invention, the polymeric detection system may be easily adapted for multi-parametric detection in solution using different fluorophores attached to ss-DNA probes or using micro-arrays on solid supports.

In an embodiment, the present invention relates to a novel nucleic acid detection system comprising an anionic oligonucleotide probe, a water-soluble conjugated affinitychromic cationic polymeric transducer, and an intrinsic photonic amplification mechanism. The water-soluble conjugated affinitychromic cationic polymeric transducer also serves as a localized counter-ion promoting specific hybridization. In an embodiment of the present invention, the cationic polymeric transducer comprises a water-soluble conjugated affinity-chromic cationic polythiophene (FIG. 1; Polymer 1). Such a cationic polythiophene has been previously described and was prepared following known literature procedures.[10, 13]

The water-soluble conjugated cationic polythiophene as used herein exhibits affinitychromic properties (changes of the UV-visible absorption spectrum upon binding which come from conformational changes), when put in the presence of single-stranded (ss) or double-stranded (ds) nucleic acids[10, 13]. For instance, Polymer 1 in aqueous media provides a yellow solution ($\lambda_{max}$=397 nm) corresponding to a random-coil, poorly conjugated conformation of the polythiophene. When a stoichiometric amount (on a repeat unit basis) of a 20-mer unlabeled capture probe (i.e. X1: 5'-CAT-GATTGMCCATCCACCA-3') is added, the mixture turns red ($\lambda_{max}$=527 nm), corresponding to a planar, highly conjugated aggregated form of the polythiophene. This is indicative of the formation of a neutral so-called "duplex" (capture strand) between the cationic polythiophene and the anionic oligonucleotide probe. Upon addition of a complementary oligonucleotide (i.e. Y1: 3'-GTACTAACTTGGTAGGTGGT-5') to the capture strand, a triplex is formed. Formation of the triplex results in a further color change of the mixture, with the mixture returning to a yellow color ($\lambda_{max}$=421 nm; FIG. 1A, a). Slight changes in the absorption spectra are observed (data not shown) with the addition of oligonucleotides having two mismatches (i.e. Y2: 3'-GTACTMCTTCGAAGGTGGT-5') or as little as one mismatch (i.e. Y3: 3'-GTACTAACTT CGTAGGTGGT-5').

Fluorometric detection of nucleic acids is also possible using the novel DNA detection system of the present invention. Fluorometric detection is possible because the fluorescence of poly(3-alkoxy-4-methylthiophene)s is quenched in the planar aggregated form (duplex), whereas the yellow triplex form is fluorescent, having an emission maximum at 530 nm (FIG. 1B, a) when excited at 420 nm.

The specificity and sensitivity of the polymeric transducer was further improved by combining it with capture probes labeled with a fluorophore (e.g. Alexa Fluor 546) in order to induce Förster Resonance Energy Transfer (FRET). Using this improved transducer, the stoichiometric duplex still exhibits a red color (FIG. 1A, b) and quenched fluorescence (FIG. 1B, b). When this duplex is hybridized with its complementary oligonucleotide, a new absorption band can be observed at 420 nm, corresponding to the formation of a triplex (FIG. 1A, c). The emission maximum of the resulting triplex (530 nm) overlaps neatly with the absorption spectrum of the fluorophore (Alexa Fluor 546) which has absorption bands at 516 and 556 nm (FIG. 1A, c) and which then emits at longer wavelengths (emission maximum at 572 nm; FIG. 1B, c). When a non-complementary or mismatched DNA is added to the duplex, no color change is detected: the duplex solution remains red. This is indicative of an inhibition of the FRET mechanism. Consequently, the fluorescence intensity as measured with the perfect complementary ss-DNA strand (identical experimental conditions) is always higher as compared to those obtained with targets having one or two mismatches.

Figure 3:
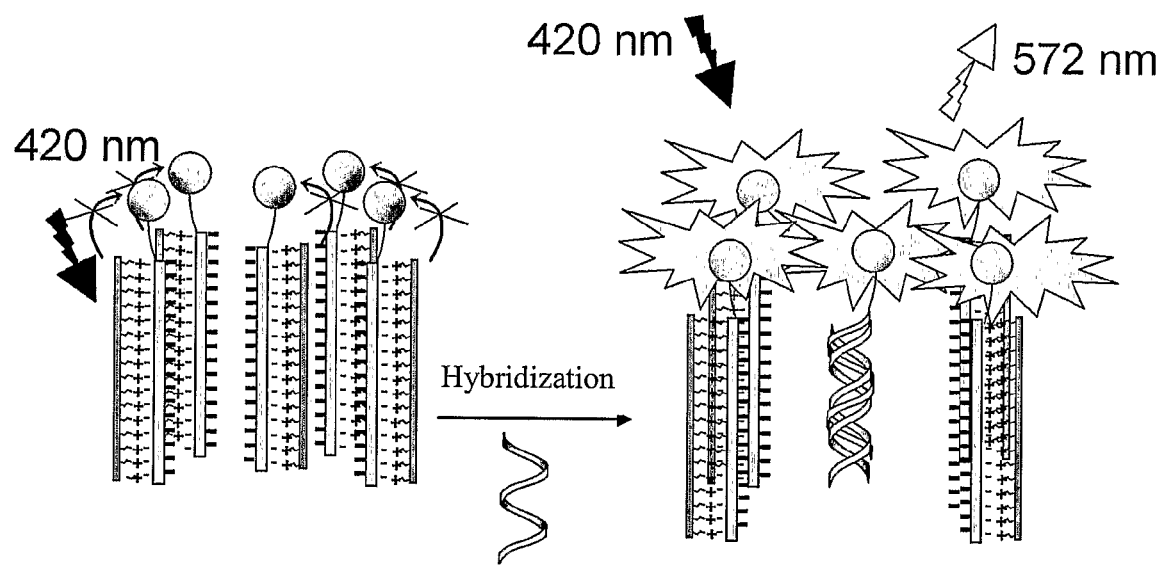
FIG. 3 illustrates a schematic description of the signal amplification detection mechanism of the present invention, based on conformational changes of the cationic polythiophene and energy transfer for ultrasensitive, selective, and rapid DNA detection.

Surprisingly, starting with a large amount of stoichiometric duplex probes (ca. $10^{10}$ copies), as little as about 30 copies of a 20-mer oligonucleotide could be easily and specifically detected in a sample (3 mL) using the present novel DNA detection system. Moreover, perfectly complementary targets could still be distinguished at such low concentrations from sequences having two or merely one mismatch. The detection limit as calculated from these data using a custom blue-LED fluorimeter was a mere 5 copies in a volume of 3 mL, which equates to a concentration of 3 zM ($3 \times 10^{-21}$ M). A somewhat higher detection limit (30 copies in a volume of 3 mL; 18 zM) was obtained using a commercial spectrofluorometer (Varian Cary Eclipse). The use of capture probes labeled with a fluorophore in the DNA detection system of the present invention, provides a "turn-on" amplified signal[15] that can be described as a "super-lighting" process or "fluorescence chain reaction" (FCR). As illustrated in FIG. 3, it is believed that this highly efficient energy transfer is mainly due to the formation of aggregates of duplexes in solution prior to the introduction of the target.[10, 13] These aggregates would then give rise to a very efficient energy transfer between a given triplex and a large number of neighboring Alexa Fluor chromophores. Indeed, this chromophore shows a Stokes shift of only 16 nm and a fluorescence quantum yield of 95% with a fluorescence lifetime of 3.6 nsec. These are excellent parameters for highly efficient inter-molecular energy transfer among aggregated conjugated molecules[16-20].

In an embodiment of the present invention, the novel nucleic acid detection system can also be used for the ultra sensitive detection of ds-DNA. When capture probes labelled with a fluorophore are used in order to induce signal amplification, extremely low concentration levels of ds-DNA can be detected. Because the probe-to-target hybridization reaction is in competition with rehybridization of the ds-DNA, most previously reported direct DNA detection techniques rely on the availability of the target sequence as ssDNA. In the case of the polythiophene transducer used in the present invention, previous studies have shown that the presence of non-complementary ds-DNA may lead to false positive signals since the polythiophene transducer has a higher affinity, as compared to the ss-DNA probes for ds-DNA.[10, 13]

Experimental conditions have been elaborated that selectively enhance the recognition reaction between the DNA capture probe and the DNA target. Specifically, in pure water at 65° C., all denatured DNA material remains denatured and hybridization essentially only occurs with the labeled ss-DNA probes in the duplexes, promoted by the electrostatically-bound cationic polythiophene transducer which also serves as a localized counter-ion for the negative charges of the phosphate moieties.

Figure 2:
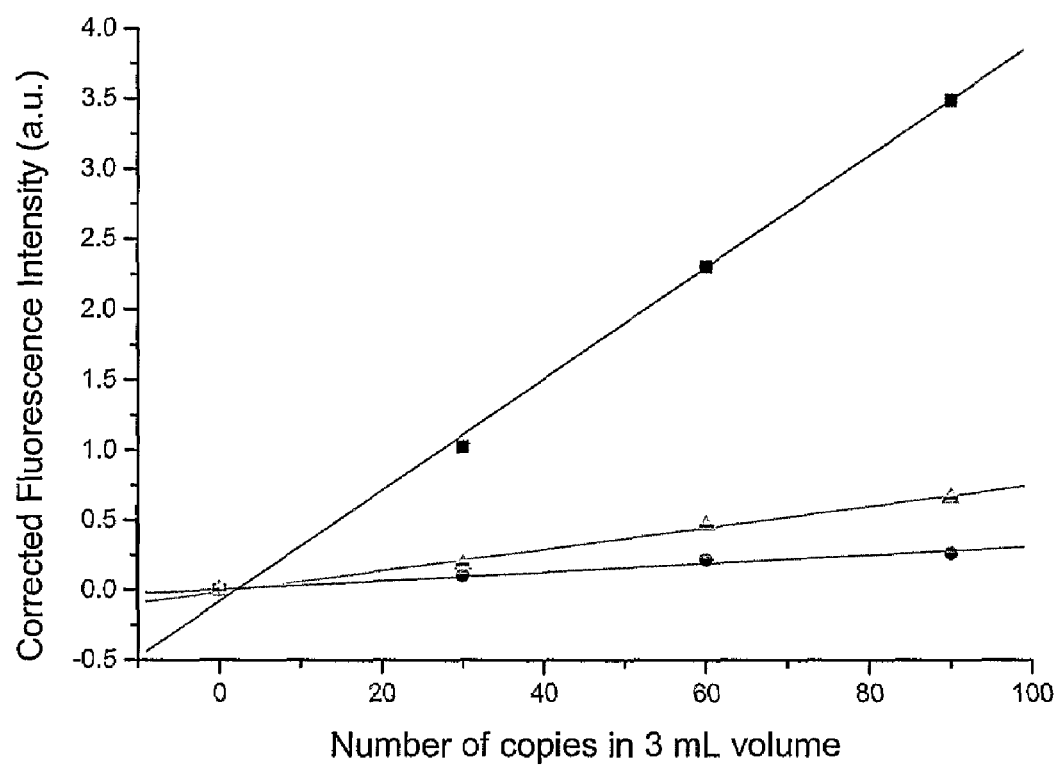
FIG. 2 illustrates the corrected fluorescence intensity (after subtraction of the signal due to initial duplex) measured at 572 nm in water at 55° C., with excitation at 420 nm, as a function of the number of 20-mer oligonucleotide target copies: (squares) perfect match; (circles) two mismatches; (triangles) one mismatch.

In an embodiment of the present invention, the novel nucleic acid detection system can also be used to distinguish single nucleotide polymorphisms (SNPs) in non amplified human genomic DNA samples. In a further embodiment, the novel nucleic acid detection system can be used to distinguish disease associated SNPs in non amplified human genomic DNA samples. The high specificity and sensitivity of (FRET)-enhanced detection, combined with the ability of the polythiophene transducer to promote hybridization in otherwise unfavorable conditions, allows disease-associated single nucleotide polymorphisms (SNPs) in non amplified human genomic DNA samples to be distinguished. FIG. 4A shows calibration curves obtained by testing normal (i.e. wild type) human genomic DNA, with probe sequences complementary to the wild type (TAN 101: 5'-CCG GTG AGT ATC TGG-3') and with mutated (TAN 100: 5'-CCG GTG AAT ATC TGG-3') sequences. Similarly, FIG. 4B shows calibration curves obtained by testing mutated human genomic DNA (from ill patients), with probe sequences complementary to the wild type (TAN 101: 5'-CCG GTG AGT ATC TGG-3'), and with mutated (TAN 100: 5'-CCG GTG AAT ATC TGG-3') sequences. This data was obtained in approximately 5 minutes, illustrating the ease and rapidity with which the nucleic acid detection system of the present invention allows wild-type DNA to be distinguished approximately from mutated DNA. The nucleic acid detection system of the present invention allows for the detection of a single nucleotide polymorphism (SNP) in an entire genome, without prior amplification or enrichment of the target, and at concentration levels similar to those achieved with 20-mer oligonucleotides (FIG. 2). For example, although two 15-mer oligonucleotides were uniquely designed to probe tyrosinemia in the human genome, numerous loci presenting only one mismatch with these probes are known to exist in nature, notably at the extremities of the gene. Surprisingly, no significant hybridization signal could be detected using these non-specific target sequences.

Very stringent hybridization conditions are obtained by carrying out the hybridization reactions in pure water at 65° C. Under these stringent conditions, the cationic polythiophene transducer localized on the capture probe is the only counter-ion available to neutralize the phosphate backbone of the nucleic acids, thus allowing for excellent specificity. These features suggest broad applicability of the nucleic acid detection system of the present invention. In an embodiment, the nucleic acid detection system could be used to selectively detect nucleic acid sequences in complex mixtures.

Figure 5:
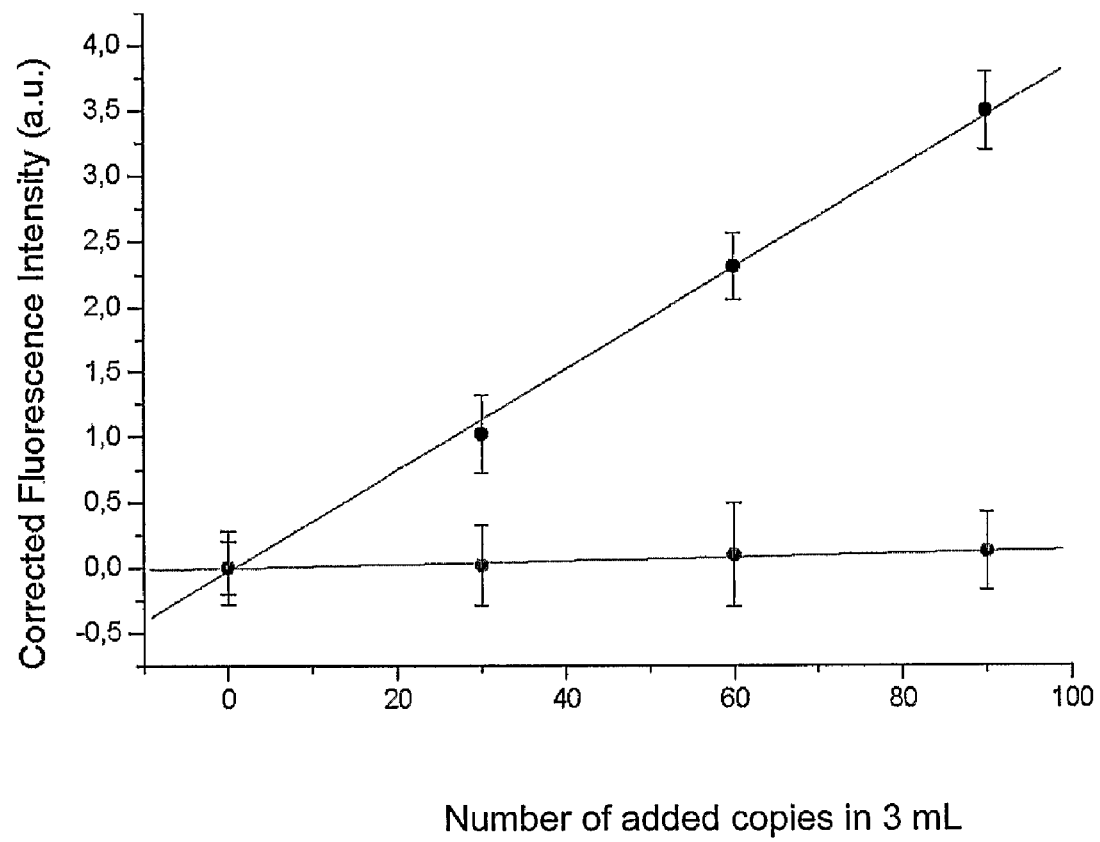
FIG. 5 illustrates the corrected fluorescence intensity (after subtraction of the signal due to the initial duplex) measured at 572 nm, with excitation at 420 nm in pure water at 55° C., as a function of the number of 20-mer oligonucleotide target copies: (dark line) perfect match; (light line) two mismatches.

Experiments similar to those described in relation to FIG. 2 were performed on a commercial spectrofluorometer (Varian Cay Eclipse). Highly sensitive and selective detection of ss-oligonucleotides was also obtained, as shown in FIG. 5. In this case, the limit of detection is about 30 copies in 3 mL of pure water at 55° C.

The applicability of the method to various kinds of genetic material, i.e. PCR products (amplicons) and human genomic DNA, was also tested. Although the method of the present invention aims at eliminating the need for PCR amplification, amplicon products are an obvious choice because they are widely used in biotechnology research. Furthermore, they are also a model of double-stranded DNA, and thus serve as a good intermediate between oligonucleotides and the complete human genome. For this study, probe X1+AF546 was used (see FIG. 2) with C. albicans and C. dubliniensis amplicons.

Figure 6:
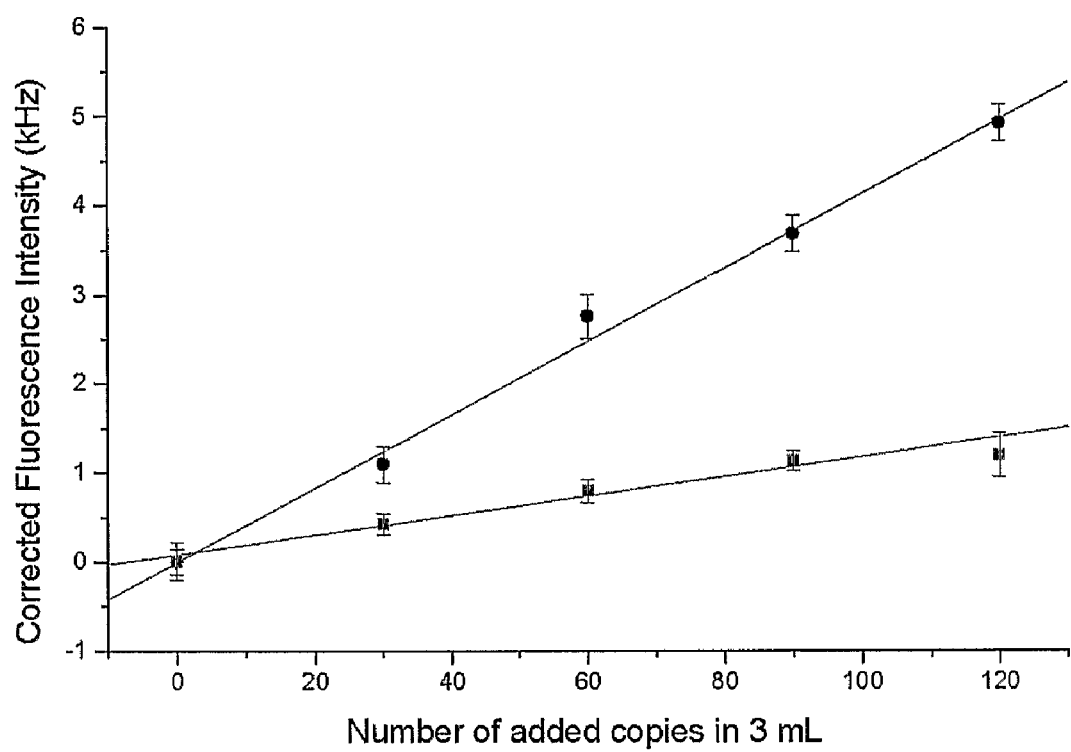
FIG. 6 illustrates the corrected fluorescence intensity (after subtraction of the signal due to the initial duplex) measured at 572 nm, with excitation at 420 nm in pure water at 65° C., as a function of the number of 150 bp amplicon target copies; (dark line) perfect match (*C. albicans* amplicon); (light line) two mismatches (*C. dubliniensis* amplicon)

FIG. 6 was obtained using the same procedure as described above. This Figure shows that the method of the present invention can readily distinguish perfectly matched amplicons from those differing by only two nucleotides in a 150 nucleotide-long ds-DNA. This high degree of selectivity was obtained using the intrinsic signal amplification process described above and optimized experimental conditions (pure water at 65° C.).

For human DNA, and using the same calculations and database as those described in the experimental section, the method of the present invention was tested using another probe sequence, this time specific to the E357X mutation, which is also reported as causing hereditary tyrosinemia [ref 21 in the text]. New probes specific to the E357X mutation, i.e. TAN 102a: 5'-/5Alex546N/AGGAGCCAGAAAACT-TCG-3 and TAN 103a:'5'-/5Alex546N/AGGAGCCAT-AAAACTTCG-3 were specifically designed and synthesised by IDT DNA technologies Inc. In order to test the applicability of the method of the present invention to human genomic DNA extracted using various extraction techniques human genomic DNA extracted using another, broadly used method, namely the Promega protocol, was chosen.

Figure 4:
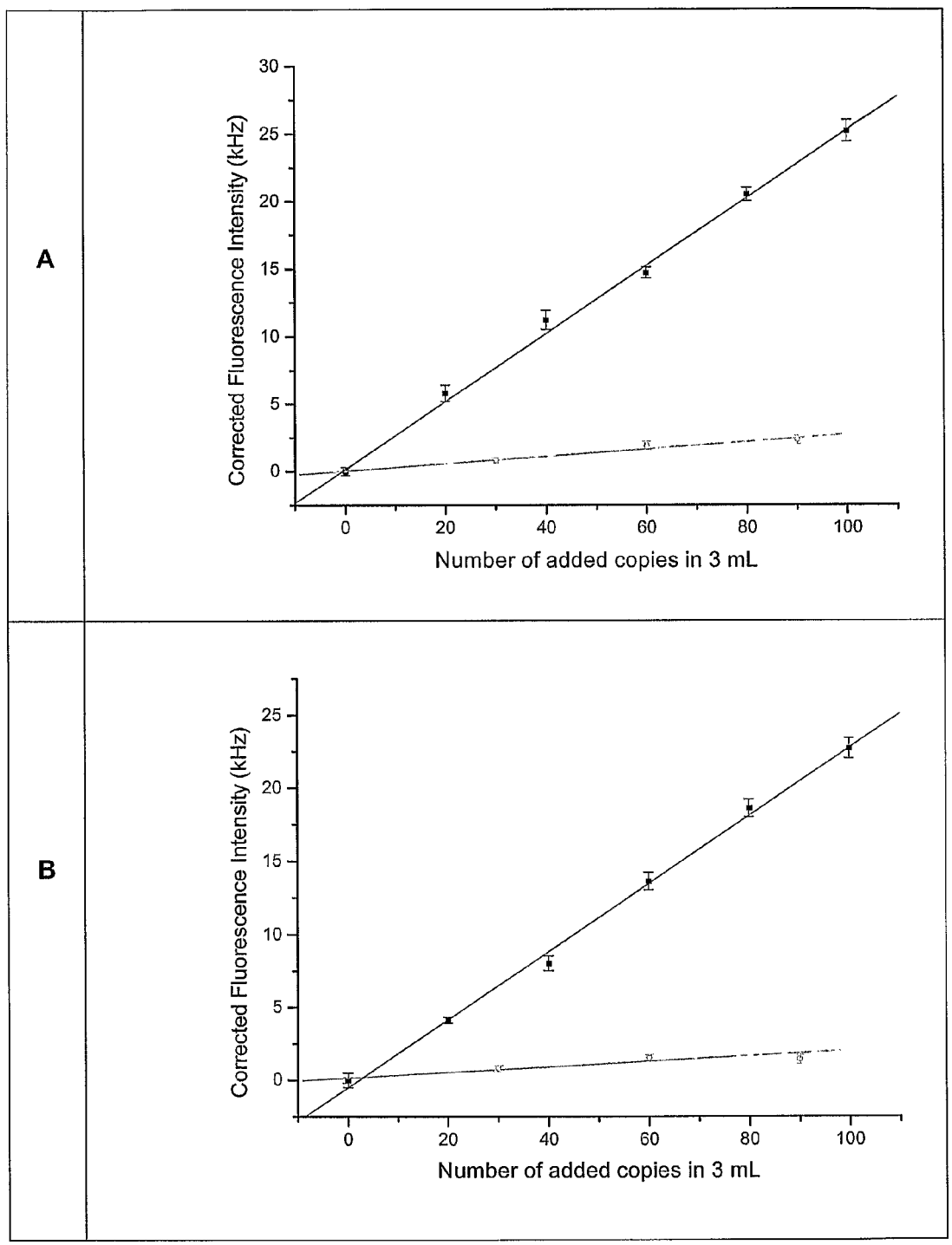
FIG. 4 illustrates: A. Corrected fluorescence intensity (after subtraction of the signal due to initial duplex) measured at 572 nm, with excitation at 420 nm, as a function of the number of genomic DNA copies: (dark line) TAN 101+ wild type genomic DNA (perfect match); (light line) TAN 100+ wild type genomic DNA (one mismatch). B. Corrected fluorescence intensity (after subtraction of the signal due to initial duplex) measured at 572 nm, with excitation at 420 nm, as a function of the number of genomic DNA copies: (dark line) TAN 101+ mutated genomic DNA (perfect match); (light line) TAN 100+ mutated genomic DNA (one mismatch)
Figure 7:
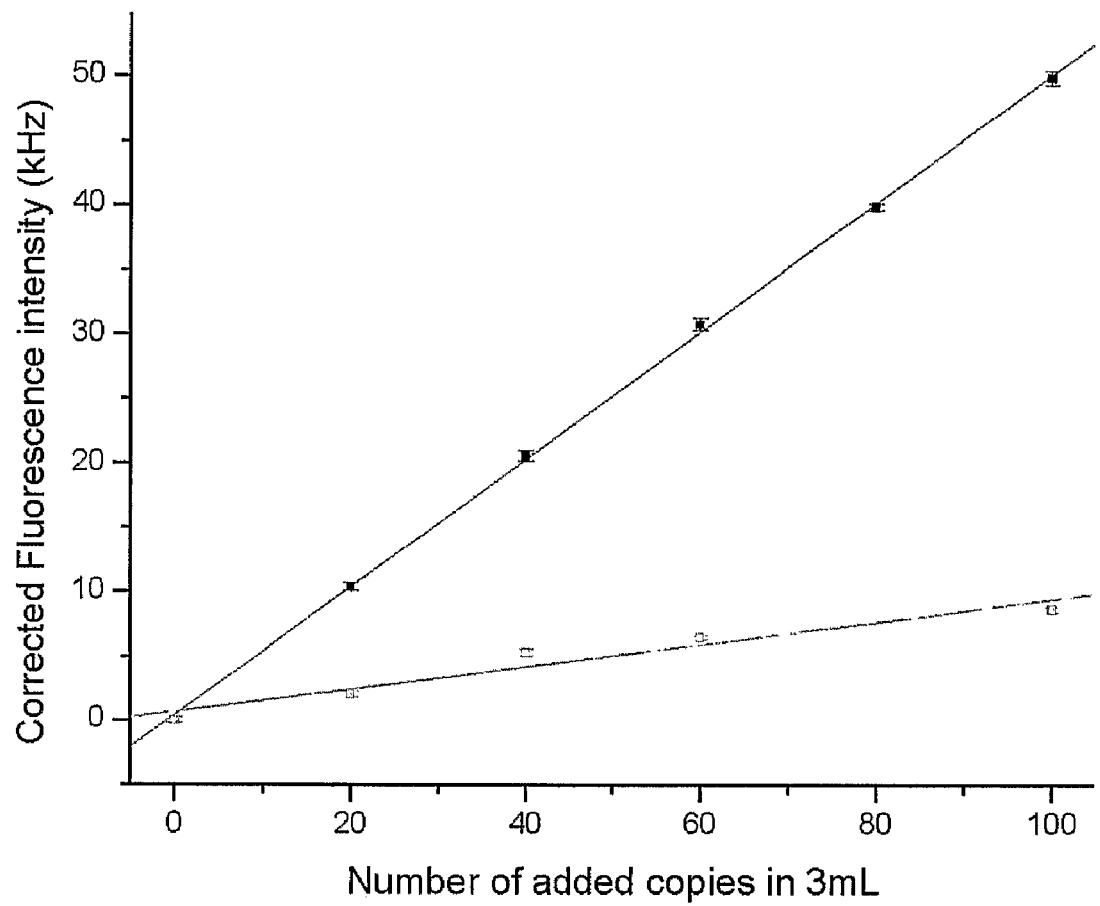
FIG. 7 illustrates the corrected fluorescence intensity (after subtraction of the signal due to the initial duplex) measured at 572 nm, with excitation at 420 nm in pure water at 65° C., as a function of the number of genomic DNA copies: (dark line) TAN 102a+ wild type genomic DNA (perfect match); (light line) TAN 103a+ wild type genomic DNA (one mismatch).

FIG. 7 was obtained using the same experimental protocol as described above. The curves obtained with the TAN102a and TAN103a probes specific to the E357X mutation are very similar to those obtained for the IVS12 mutation (FIG. 4). The higher detection sensitivity in the present case is due to the increased number of polymeric chromophoric units when working with longer, 18-mer probes (as compared with the 15-mer probes used for the IVS12 mutation). This further example of SNP detection in total, non-amplified human genomic DNA confirms the capability of the method of the present invention to selectively and specifically detect a few copies of DNA strands in the presence of a much greater amount of non-specific DNA material.

Although the present invention has been described hereinabove by way of preferred embodiments thereof, it can be modified without departing from the spirit, scope and the nature of the subject invention, as defined in the appended claims.

REFERENCES

1. Daar, A. S. et al. Top ten biotechnologies for improving health in developing countries. Nat. Genet. 32, 229-232 (2002).
2. Fodor, S. P. A. et al. Light-directed spatially addressable parallel chemical synthesis. Science 251, 767-773 (1991).
3. Tyagi, S. & Kramer, F. R. Molecular beacons: probes that fluoresce upon hybridization. Nat. Biotechnology 14, 303-308 (1996).
4. Leclerc, M. Optical and electrochemical transducers based on functionalized conjugated polymers. Adv. Matter. 11, 1491-1498 (1999).
5. McQuade, D. T., Pullen, A. E. & Swager, T. M. Conjugated polymer-based chemical sensors. Chem. Rev. 100, 2537-2574 (2000).
6. Drummond, T. G., Hill, M. G. & Barton, J. K. Electrochemical DNA sensors. Nat. Biotechnology 21, 1192-1199 (2003).
7. Nam, J. M., Stoeva, S. I. & Mirkin, C. A. Bio-bar-code-based DNA detection with PCR-like sensitivity. J. Am. Chem. Soc. 126, 5932-5933 (2004).
8. Liu, R. H., Yang, J., Lenigk, R., Bonanno, J. & Grodzinski, P. Self-contained, fully integrated biochip for sample preparation, polymerase chain reaction amplification, and DNA microarray detection. Anal. Chem. 76, 1824-1831 (2004).
9. Saiki, R. K. et al. Enzymatic amplification of beta-globin genomic sequences and restriction site analysis from diagnostic sickle-cell anemia. Science 230, 1350-1354 (1985).
10. Ho, H. A. et al. Colorimetric and fluorometric detection of nucleic acids using cationic polythiophene derivatives. Angew. Chem. Int Ed. 41, 1548-1551 (2002).
11. Gaylord, B. S., Heeger, A. J. & Bazan, G. C. DNA detection using water-soluble conjugated polymers and peptide nucleic acid probes. Proc. Natl. Acad. Sci. U.S.A. 99, 10954-10957 (2002).
12. Nilson, K. P. R. & Inganäs, O. Chip and solution detection of DNA hybridization using a luminescent zwitterionic polythiophene derivative. Nat. Matter. 2, 419-424 (2003).
13. Doré, K. et al. Fluorescent polymeric transducer for the rapid, simple, and specific detection of nucleic acids at the zeptomole level. J. Am. Chem. Soc. 126, 4240-4244 (2004).
14. Liu, B. & Bazan, G. C. Homogeneous fluorescence-based DNA detection with water-soluble conjugated polymers. Chem. Mater. 16, 4467-4476 (2004).
15. McQuade, D. T., Hegedus, A. H. & Swager, T. M. Signal amplification of a "turn-on" sensor: Harvesting the light captured by a conjugated polymer. J. Am. Chem. Soc. 122, 12389-12390 (2000).
16. Levitsky, I. A., Kim, J. & Swager, T. M. Energy migration in a poly(phenylene ethynylene): Determination of interpolymer transport in anisotropic Langmuir-Blodgett films. J. Am. Chem. Soc. 121, 1466-1472 (1999).
17. Nguyen, T.-Q., Wu, J., Doan, V., Schwartz, B. J. & Tolbert, S. H. Control of energy transfer in oriented conjugated polymer-mesoporous silica composites. Science 288, 652-656 (2000).
18. Kim, J. & Swager, T. M. Control of conformational and interpolymer effects in conjugated polymers. Nature 411, 1030-1034 (2001).
19. Beljonne, D. et al. Interchain vs. intrachain energy transfer in acceptor-capped conjugated polymers. Proc. Natl. Acad. Sci. U.S.A. 99, 10982-10987 (2002).
20. Chen, L. et al. Highly sensitive biological and chemical sensors based on reversible fluorescence quenching in a conjugated polymer. Proc. Natl. Acad. Sci. U.S.A. 96, 12287-12292 (1999).
21. St-Louis, M. & Tanguay, R. M. Mutations in the fumarylacetoacetate hydrolase gene causing hereditary tyrosinemia type I: overview. Hum. Mutat. 9, 291-299 (1997).
22. Phaneuf, D., Lambert, M., Laframboise R., Mitchell G., Lettre F. & Tanguay R. M. Type 1 hereditary tyrosinemia. Evidence for molecular heterogeneity and identification of a causal mutation in a French Canadian patient. J. Clin. Invest. 90, 1185-1192 (1992).
23. United States Patent Application Publication No. US 2005/0003386 A1 (Jan. 6, 2005) (Bazan et al.)
24. United States Patent Application Publication No. US 2004/0219556 A1 (Nov. 4, 2004) (Bazan et al.)
25. United States Patent Application Publication No. US 2004/0142344 A1 (Jul. 22, 2004) (Bazan et al.)
26. United States Patent Application Publication No. US 2004/0142206 A1 (Jul. 22, 2004)

What is claimed is:

1. A nucleic acid detection system comprising:
an anionic oligonucleotide probe labeled with a fluorophore;
and
a water-soluble affinitychromic cationic polythiophene that interacts with said probe to form a neutral duplex, wherein said neutral duplex exhibits changes in its absorption spectrum in the presence of a target polynucleotide.

2. A kit comprising a vessel or vessels containing:
an anionic oligonucleotide probe labeled with a fluorophore;
and
a water-soluble affinitychromic cationic polythiophene that interacts with said probe to form a neutral duplex, wherein said neutral duplex exhibits changes in its absorption spectrum in the presence of a target polynucleotide.

3. An article of manufacture comprising:
a vial containing an anionic oligonucleotide probe labeled with a fluorophore and containing an affinitychromic cationic polythiophene that interacts with said probe to form a neutral duplex, wherein said neutral duplex exhibits changes in its absorption spectrum in the presence of a target polynucleotide;
or
packaged together, a vial containing an anionic oligonucleotide probe labeled with a fluorophore, and a vial containing an affinitychromic cationic polythiophene that interacts with said probe to form a neutral duplex, wherein said neutral duplex exhibits changes in its absorption spectrum in the presence of a target polynucleotide.

4. A method of measuring the presence of a target polynucleotide comprising:
providing an anionic oligonucleotide probe labeled with a fluorophore and an affinitychromic cationic polythiophene that interacts with said probe to form a neutral duplex, wherein said neutral duplex exhibits changes in its absorption spectrum in the presence of a target polynucleotide;
contacting a target polynucleotide with said neutral duplex;
and
measuring the changes in the absorption spectrum of said neutral duplex in the presence of said target polynucleotide in order to quantify or analyse the complementarity of said target polynucleotide relative to said probe.

5. An assay based on the method of claim 4.

6. The nucleic acid detection system as defined in claim 1, wherein said target polynucleotide is derived from the human genome, a bacterial source or a viral source, or is an amplicon.

7. The nucleic acid detection system as defined in claim 6, wherein said target polynucleotide is denatured prior to its use in the system.

8. The kit as defined in claim 2, wherein said target polynucleotide is derived from the human genome, a bacterial source or a viral source, or is an amplicon.

9. The kit as defined in claim 8, wherein said target polynucleotide is denatured prior to its use in the system.

10. The article of manufacture as defined in claim 3, wherein said target polynucleotide is derived from the human genome, a bacterial source or a viral source, or is an amplicon.

11. The article of manufacture as defined in claim 10, wherein said target polynucleotide is denatured prior to its use in the system.

12. The method as defined in claim 4, wherein said target polynucleotide is derived from the human genome, a bacterial source or a viral source, or is an amplicon.

13. The method as defined in claim 12, wherein said target polynucleotide is denatured prior to its use in the system.

* * * * *

SEQUENCE LISTING

<160> NUMBER OF SEQ ID NOS: 10

<210> SEQ ID NO 1
<211> LENGTH: 26
<212> TYPE: DNA
<213> ORGANISM: Artificial
<220> FEATURE:
<223> OTHER INFORMATION: Primer Ecal61 (5'-3')

<400> SEQUENCE: 1
caagaaggtt ggttacaacc caaaga                                              26

<210> SEQ ID NO 2
<211> LENGTH: 26
<212> TYPE: DNA
<213> ORGANISM: Artificial
<220> FEATURE:
<223> OTHER INFORMATION: Primer Ecal84 (5'-3')

<400> SEQUENCE: 2
aggtcttacc agtaacttta ccggat                                              26

<210> SEQ ID NO 3
<211> LENGTH: 20
<212> TYPE: DNA
<213> ORGANISM: Artificial
<220> FEATURE:
<223> OTHER INFORMATION: Capture probe (X1:5'-3')

<400> SEQUENCE: 3
catgattgaa ccatccacca                                                     20

<210> SEQ ID NO 4
<211> LENGTH: 20
<212> TYPE: DNA
<213> ORGANISM: Artificial
<220> FEATURE:
<223> OTHER INFORMATION: Complementary oligonucleotide (Y1:3'-5')

<400> SEQUENCE: 4
gtactaactt ggtaggtggt                                                     20

<210> SEQ ID NO 5
<211> LENGTH: 20
<212> TYPE: DNA
<213> ORGANISM: Artificial
<220> FEATURE:
<223> OTHER INFORMATION: Oligonucleotide having two mismatches
      (Y2:3'-5')

<400> SEQUENCE: 5
gtactaactt cgaaggtggt                                                     20

<210> SEQ ID NO 6
<211> LENGTH: 20
<212> TYPE: DNA
<213> ORGANISM: Artificial
<220> FEATURE:
<223> OTHER INFORMATION: Oligonucleotide having one mismatch (Y3:3'-5')

<400> SEQUENCE: 6
gtactaactt cgtaggtggt                                                     20

<210> SEQ ID NO 7
<211> LENGTH: 15

-continued

```
<212> TYPE: DNA
<213> ORGANISM: Artificial
<220> FEATURE:
<223> OTHER INFORMATION: Probe sequences complementary to the wild type
      (TAN 01:5'-3')

<400> SEQUENCE: 7
ccggtgagta tctgg                                                      15

<210> SEQ ID NO 8
<211> LENGTH: 15
<212> TYPE: DNA
<213> ORGANISM: Artificial
<220> FEATURE:
<223> OTHER INFORMATION: Probe with mutated sequences (TAN 100:5'-3')

<400> SEQUENCE: 8
ccggtgaata tctgg                                                      15

<210> SEQ ID NO 9
<211> LENGTH: 18
<212> TYPE: DNA
<213> ORGANISM: Artificial
<220> FEATURE:
<223> OTHER INFORMATION: Probe specific to the E357X mutation 5Alex546N
      (TAN 102a:5'-3')

<400> SEQUENCE: 9
aggagccaga aaacttcg                                                   18

<210> SEQ ID NO 10
<211> LENGTH: 18
<212> TYPE: DNA
<213> ORGANISM: Artificial
<220> FEATURE:
<223> OTHER INFORMATION: Probe specific to the E357X mutation 5Alex546N
      (TAN 103a:5'-3')

<400> SEQUENCE: 10
aggagccata aaacttcg                                                   18
```